United States Patent [19]

Dauth et al.

[11] Patent Number: 5,496,961
[45] Date of Patent: Mar. 5, 1996

[54] TRIAZENE OXIDE-TRANSITION METAL COMPLEXES AS HYDROSILYLATION CATALYSTS

[75] Inventors: Jochen Dauth, Burghausen; Josef Wolferseder, Altoetting; Bernward Deubzer, Burghausen, all of Germany

[73] Assignee: Wacker-Chemie GmbH, Munich, Germany

[21] Appl. No.: 437,830

[22] Filed: May 10, 1995

[30] Foreign Application Priority Data

Jul. 1, 1994 [DE] Germany ............................ 44 23 195.4

[51] Int. Cl.$^6$ .................................. C07F 7/08; C07F 7/10; C07F 15/00
[52] U.S. Cl. ............................. 556/9; 556/12; 556/136; 556/137; 556/479; 528/14; 528/15; 546/4; 546/12; 546/14; 549/3; 549/206; 549/212; 549/214; 548/402; 534/551; 534/552; 502/152; 502/158; 502/167
[58] Field of Search ............................ 556/9, 12, 136, 556/137, 479; 528/15, 14; 546/4, 12, 14; 549/214, 3, 206, 212; 534/551, 552; 548/402; 502/152, 158, 167

[56] References Cited

U.S. PATENT DOCUMENTS 3,814,730  6/1974  Karstedt .
5,426,200  6/1995  Dauth et al. ...................... 556/9

OTHER PUBLICATIONS

R. L. Dutta, R. Sharma; J. Sci. Ind. Res., 40(11) (1981) 715–737.

D. N. Purohit et al.; Rev. Anal. Chem., 11(3–4), 269 (1992).

*Primary Examiner*—Paul F. Shaver
*Attorney, Agent, or Firm*—Martin Connaughton

[57] ABSTRACT

Organosilicon compounds having Si-bonded hydrogen atoms are reacted with organic compounds having aliphatic multiple bonds in the presence of triazene oxide-transition metal complexes. The triazene oxide-transition metal complexes are activated by heating at temperatures of from 50° C. to 250° C. and/or by irradiation with light.

4 Claims, No Drawings

TRIAZENE OXIDE-TRANSITION METAL COMPLEXES AS HYDROSILYLATION CATALYSTS

FIELD OF INVENTION

The present invention relates to a process for hydrosilylation in the presence of triazene oxide-transition metal complexes, crosslinkable organopolysiloxane compositions containing triazene oxide-transition metal complexes triazene oxide-platinum complexes and a process for preparing the triazene oxide-platinum complexes.

BACKGROUND OF INVENTION

Triazene oxide-transition metal complexes are described in, R. L. Dutta, R. Sharma; J. Sci. Ind. Res., 40(11) (1981) 715 and D. N. Purohit et al., Rev. Anal. Chem., 11(3–4), 269 (1992). Triazene oxide-platinum complexes are not described.

It is known that the addition of Si-bonded hydrogen to an aliphatic multiple bond, usually termed hydrosilylation, can be promoted by means of catalysts, in particular platinum compounds. Reference may be made to U.S. Pat. No. 3,814,730. These catalysts have a low activation energy and frequently have to be inhibited in additional crosslinking systems.

SUMMARY OF INVENTION

It is the object of the present invention to provide catalysts which have a high activation energy, requires little, if any inhibition in addition-crosslinking systems, but after activation promote the addition of Si-bonded hydrogen to an aliphatic multiple bond.

The present invention provides a process for reacting organosilicon compounds having Si-bonded hydrogen atoms with organic compounds having aliphatic multiple bonds in the presence of triazene oxide-transition metal complexes of the formula $$M(ANNNOR^1)_a X_b \qquad (1)$$

where
M is Pt, Pd, Rh, Ru, Os or Ir,
$R^1$ is a monovalent, unsubstituted or substituted hydrocarbon radical having from 1 to 18 carbon atoms per radical, a radical of the formula $-SiR^2_c(OR^2)_{3-c}$ or A,
$R^2$ is identical or different and is an alkyl radical having from 1 to 8 carbon atoms per radical,
A is identical or different and is a radical of the formula

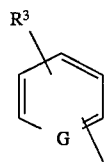

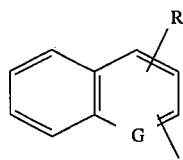

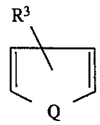

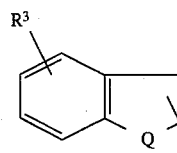

or

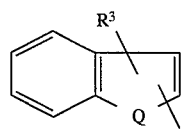

G is CH or N,
Q is S, O or NH,
$R^3$ is a monovalent, unsubstituted or substituted hydrocarbon radical having from 1 to 12 carbon atoms per radical or is a radical of the formula $-F$, $-Cl$, $-Br$, $-I$, $-H$, $-NH_2$, $-NR^2{}_2$, $-NO_2$, $-OH$, $-OR^2$, $-SH$, $-CN$, $-COOH$, $-COCl$, $-CONH_2$, $-COR^2$, $-CHO$, $-SO_2NHR^2$, $-SO_3H$, $-SO_2Cl$ or $-R^4-SiR^2{}_c(OR^2)_{3-c}$,
$R^4$ is a divalent hydrocarbon radical having from 1 to 8 carbon atoms per radical,
$R^2$ is identical or different and is an alkyl radical having from 1 to 8 carbon atoms per radical,
X is identical or different and is a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane, 1,3-divinyl-1,1,3,3-tetramethyldisiloxane, ethylene and diphenylacetylene.
a is 1, 2, 3 or 4
b is 0 or an integer from 1 to 6 and
c is 0, 1, 2 or 3,
wherein the triazene oxide-transition metal complexes are activated by heating at temperatures of from 50° C to 250° C and/or by irradiation with light.

Examples of radicals $R^1$ are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl and cyclohexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical, dodecyl radicals such as the n-dodecyl radical; and octadecyl radicals such as n-octadecyl radical; cycloalkyl radicals such as the cyclohexyl radical; alkenyl radicals such as the vinyl, 1-propenyl, 1-butenyl, 2-butenyl, allyl, isobutenyl, 1-pentenyl and 2-methyl-1-butenyl radical; alkynyl radical such as the ethynyl, propargyl, 1-propynyl and 1-butynyl radical, and aralkyl radicals such as the benzyl radical and the α- and β-phenylethyl radical; with alkyl radicals being preferred.

Examples of substituted hydrocarbon radicals $R^1$ are haloalkyl radicals such as the 3,3,3-trifluoro-n-propyl radical, the 2,2,2,2',2',2'-hexafluoroisopropyl radical, the heptafluoroisopropyl radical, the 3-chloro-n-propyl radical, 2-ethyl bromide and 3-propyl bromide; hydroxyalkyl radicals such as the radical of the formulae $HOCH_2CH_2OCH_2CH_2-$, $HOCH_2CH_2-$ and $CH_3CH_2CH(OH)CH_2-$; aminoalkyl radicals such as the aminomethyl and aminoethyl radical; carboxyalkyl radicals such as the radicals of the formulae $-(CH_2)_7COOH$, $-(CH_2)_8COOH$ and $-CH_2COCH_2CH_2COOH$ and also their esters and amides $-(CH_2)_7COOCH_3$, $-(CH_2)_7COOC_2H_5$, $-(CH_2)_7CONH_2$, $-(CH_2)_8COOCH_3$, $-(CH_2)_8COOC_2H_5$, $-(CH_2)_8CONH_2$, a radical of the formula $-CH(COOC_2H_5)_2$; and substituted aralkyl radicals such as the substituted benzyl radical and the substituted α- and β-phenylethyl radical.

Examples of radicals $R^2$ are the examples of alkyl radicals given for the radicals $R^1$.

Examples of radicals $R^3$ are the examples of substituted and unsubstituted hydrocarbon radicals having from 1 to 12 carbon atoms per radical which have been given for the radicals $R^1$.

Examples of hydrocarbon radicals $R^4$ are linear or branched alkylene radicals such as the methylene, ethylene, propylene, 2-methylpropylene and butylene radicals.

The radicals $R^3$ are substituents of the aromatic or heteroaromatic radical A and can be located, for example when A is an aromatic six-membered ring such as the phenyl radical, in the ortho, meta or para position.

Examples of catalysts are those of the formulae
$PtANNNOR^1{}_aX_b$, where a=2 or 4 and b=2, 1 or 0,
$PdANNNOR^1{}_aX_b$, where a=1 or 2 and b=0 or 1,
$RuANNNOR^1{}_aX_b$, where a=1, 2, 3 or 4 and b=0, 1, 2 or 3,
$RhANNNOR^1{}_aX_b$, where a=1, 2 or 3 and b=0, 1 or 2,
$OsANNNOR^1{}_aX_b$, where a=3 or 4 and b=0, 1, 2 or 3,
$IrANNNOR^1{}_aX_b$, where a=1, 2, 3 or 4 and b=0, 1, 2 or 3,
where X, A and $R^1$ are as defined above.

Preferred examples of triazene oxide-transition metal complexes are those of the formulae $Pt[C_6H_5NNNOCH_3]_4$, $Pt[p-CN-C_6H_4NNNOC_6H_{11}]4$, $pt[p-H_3CO-C_6H_4NNNOC_6H_{11}]_4$. $Pt[P-CH_3(CH_2)_x-C_6H_4NNNOCH_3]_4$, 1,5-cyclooctadiene.$Pt[p-CN-C_6H_4NNNOC_6H_{11}]_2$, 1,5-cyclooctadiene.$Pt[p-CH_3O-C_6H_4NNNOCH_3]_2$, $[(C_6H_5)_3P]_3Rh[p-CN-C_6H_4NNNOC_6H_{11}]$ and $Pd[p-CH_3(CH_2)_x-C_6H_4NNNOCH_3]_2$, where x is 1, 3, 5, 7, 11 or 17, in particular 1, 5, 7 or 11, and the above mentioned triazenido complexes of platinum are more preferred.

When the triazene oxide-transition metal complexes are used as catalysts, the activation temperature depends on the triazene oxide ligand of the general formula $ANNNOR^1$ and the transition metal atom M of the respective complex. The light with which the catalysts or the invention can be activated is preferably ultraviolet light. There are a great number of commercially available lamps which emit ultraviolet light in the range from 200 to 400 nm. The activation of the catalysts of the invention can be carried out by heating at temperatures of from 50° C. to 250° C. and additionally by irradiation with light, preferably ultraviolet light.

For the purposes of the present invention, organic compounds having aliphatic multiple bonds include organic compounds having cycloaliphatic multiple bonds.

The triazene oxide-platinum complexes of formula (I) can be used in all crosslinkable organopolysiloxane compositions in which use has also been made of catalysts which promote the addition of Si-bonded hydrogen to an aliphatic multiple bond.

The invention also provides crosslinkable organopolysiloxane compositions comprising
(1) organopolysiloxanes which have radicals containing aliphatic carbon-carbon multiple bonds,
(2) organopolysiloxanes having Si-bonded hydrogen atoms, or in place of organopolysiloxane (1) and (2)
(3) organopolysiloxanes which have radicals containing aliphatic carbon-carbon multiple bonds and Si-bonded hydrogen atoms, and
(4) triazene oxide-transition metal complexes of formula (I) as catalysts.

In the present invention, radicals having aliphatic carbon-carbon multiple bonds include radicals having cycloaliphatic carbon-carbon multiple bonds.

The organopolysiloxanes (1) used, which have radicals containing aliphatic carbon-carbon multiple bonds, are preferably linear or branched organopolysiloxanes comprising units of the formula

 (II)

where
$R^5$ is a monovalent, unsubstituted or substituted hydrocarbon radical which is free of aliphatic carbon-carbon multiple bonds and has from 1 to 18 carbon atoms per radical and
$R^6$ is a monovalent hydrocarbon radical having an aliphatic carbon-carbon multiple bond and from 2 to 8 carbon atoms per radical,
n is 0, 1, 2 or 3,
m is 0, 1 or 2
and the sum n+m is 0, 1, 2 or 3, with the proviso that on average there are at least 2 radicals $R^6$ present per molecule.

The organopolysiloxanes (1) preferably have an average viscosity of from 100 to 10000 mPa.s at 25° C.

Examples of hydrocarbon radicals $R^5$ are the examples given for $R^1$ of monovalent, unsubstituted or substituted hydrocarbon radicals which are free of aliphatic carbon-carbon multiple bonds and have from 1 to 18 carbon atoms per radical.

Examples of radicals $R^6$ are alkenyl radicals such as the vinyl, 5-hexenyl, 1-propenyl, allyl, 1-butenyl and 1-pentenyl radical; and alkynyl radicals such as the ethynyl, propargyl and 1-propynyl radical.

The organopolysiloxanes (2) used, which have Si-bonded hydrogen atoms, are preferably linear, cyclic or branched organopolysiloxanes comprising units of the formula

 (III)

where
$R^5$ is as defined for formula (II),
e is 0, 1, 2 or 3,
f is 0, 1 or 2
and the sum of e+f is 0, 1, 2 or 3, with the proviso that on average there are at least 2 Si-bonded hydrogen atoms present per molecule.

The organopolysiloxanes (2) preferably have an average viscosity of from 10 to 1000 mPa.s at 25° C.

The organopolysiloxanes (3) used, which have aliphatic carbon-carbon multiple bonds and Si-bonded hydrogen atoms and can be used in place of organopolysiloxanes (1) and (2), are preferably those comprising units of formulae

 (IV)

$$R_k^5R^6SiO_{\frac{3-l}{2}} \quad (V)$$

and $$R_p^5HSiO_{\frac{3-p}{2}}, \quad (VI)$$

where
$R^5$ and $R^6$ are as defined for formula (II),
k is 0, 1, 2 or 3,
l is 0, 1 or 2,
p is 0, 1 or 2,
with the proviso that on average there are at least 2 radicals $R^6$ and on average at least 2 Si-bonded hydrogen atoms present per molecule.

Examples of organopolysiloxanes (3) are those comprising $SiO_{4/2}$, $R^5_3SiO_{1/2}$, $R^5_2R^6SiO_{1/2}$ and $R^5_2HSiO_{1/2}$ units, MQ resins, where the resins are able to contain T units ($R^5SiO_{3/2}$) and D units ($R^5_2SiO$).

The organopolysiloxanes (3) preferably have an average viscosity of from 100 to 100000 mPa.s at 25° C. or are solids having molecular weights of from 5000 to 50000 g/mole.

The triazene oxide-transition metal complexes of formula (I) are preferably used in amounts of from 1 to 1,000 ppm by weight (parts by weight per million parts by weight), preferably from 10 to 100 ppm by weight, calculated as elemental transition metal Pt, Pd, Ru, Rh, Os or Ir and based on the total weight of the organopolysiloxanes (1) and (2) or on the total weight of the organopolysiloxanes (3).

In crosslinkable organopolysiloxane compositions, inhibitors can also be used. Examples of inhibitors are 1,3-divinyl-1,1,3,3-tetramethyldisiloxane, benzotriazole, dialkylformamides, alkylthioureas, methyl ethyl ketoxime, organic or organosilicon compounds having a boiling point of at least 25° C. at 1012 mbar (abs.) and at least one aliphatic triple bond, such as 1-ethynyl-cyclohexan-1-ol, 2-methyl-3-butyn-2-ol, 3-methyl-1-pentyn-3-ol, 2,5-dimethyl-3-hexyne-2,5-diol and 3,5-dimethyl-1-hexyn-3-ol, inhibitors comprising a mixture of diallyl maleate and vinyl acetate, and monoesters of maleic acid.

Examples of organosilicon compounds having Si-bonded hydrogen atoms are silanes having one Si-bonded hydrogen atom per molecule, such as trichlorosilane, dimethylchlorosilane, dimethylethoxysilane, methyldiethoxysilane, methyldichlorosilane and triethoxysilane, and organopolysiloxanes having at least one Si-bonded hydrogen atom per molecule, such as α,ω-dihydrogen[dimethylpolysiloxane], tetramethyldisiloxane, tetramethylcyclotetrasiloxane, copolymers comprising trimethylsiloxane and methylhydrogensiloxane units, copolymers comprising trimethylsiloxane, dimethylsiloxane and methylhydrogensiloxane units, and trimethylsiloxyhydrogensilane.

Examples of organic compounds having aliphatic multiple bonds are compounds having an aliphatic carbon-carbon double bond, such as styrene, allyl glycidyl ether, allyl cyanide, allyl acetate, allylsuccinic anhydride, glycol monoallyl ether, allyl methacrylate, allylamine and cyclohexene and compounds having an aliphatic carbon-carbon triple bond, such as acetylene and butynol.

The invention also provides triazene oxide-platinum complexes of the formula $$Pt(ANNNOR^1)_aX_b \quad (VII)$$

where A, $R^1$, X, a and b are as defined for formula (I).

The preparation of triazene oxide complexes of transition metals, with the exception of the triazene oxide complexes of platinum, and the preparation of the triazene hydroxides are described in R. L. Dutta, R. Sharma; J. Sci. Ind. Res., 40(11) (1981) 715.

The invention further provides a process for preparing the triazene oxide-platinum complexes of formula (VII), wherein triazene hydroxides of the formula $$ANNNOHR^1 \quad (VIII),$$

are reacted in the presence of bases with platinum compounds of the formula $$PtX_d \quad (IX),$$

where A, $R^1$ and X are as defined for formula (I) and d is an integer from 1 to 6.

Preferred examples of triazene hydroxide ligands of the formula $ANNNOHR^1$ which can be used in the process for preparing the triazene oxide-platinum complexes are those of the formulae $C_6H_5NNNOHCH_3$, $C_6H_5NNNOHC_6H_5$, p-$CH_3O$-$C_6H_4NNNOHCH_3$, o-$CH_3O$-$C_6H_4NNNOHCH_3$, p-CN-$C_6H_4NNNOH(CH_2)_xCH_3$, p-$NO_2$-$C_6H_4NNNOHC_6H_{11}$, p-$(CH_3)_2N$-$C_6H_4NNNOH(CH_2)_xCH_3$, and in particular p-CN-$C_6H_4NNNOHC_6H_{11}$, p-Cl-$C_6H_4NNNOHC_6H_{11}$ and p-$CH_3(CH_2)_xC_6H_4NNNOHCH_3$, where x is 1, 3, 5, 7, 11 or 17, in particular 1, 5, 7 or 11.

Examples of platinum compounds of the formula $PtX_d$ which are used in the preparation of the triazene oxide-platinum complexes are $PtCl_2$, $PtI_2$, $[(C_6H_5)_3P]_2PtCl_2$, $[(C_2H_5)_3P]_2PtCl_2$, $PtCl_4$, $Pt(H_2NCH_2CH_2NH_2)Cl_2$, $Pt(NH_3)_2Cl_2$, $PtBr_2$, $PtI_2$, $H_2PtCl_6$, 1,5-cyclooctadiene·$PtCl_2$, (1,5-cyclooctadiene)$_2$Pt, 1,3-divinyl-1,1,3,3-tetramethyldisiloxaneplatinum complex (e.g. $Pt_2$]1,3-divinyl-1,1,3,3-tetramethyldisiloxane]$_3$), bis(diphenylacetylene)Pt, with $PtCl_4$, 1,5-cyclooctadiene·$PtCl_2$, $PtI_2$ and 1,3-divinyl-1,1,3,3-tetramethyldisiloxaneplatinum complex being preferred.

Examples of bases which are used in the preparation of the triazene oxide-platinum complexes are n-butyllithium, tiethylamine, piperidine, pyridine, $NaOCH_3$ and $NaNH_2$, with n-butyllithium and triethylamine being preferred.

The process for preparing the triazene oxide-platinum complexes is preferably carried out in the presence of organic solvents such as n-hexane, toluene, methylene chloride, chloroform, acetone or tetrahydrofuran, but it can also be carried out in the presence of a mixture of water and organic solvent such as methanol, ethanol, isopropanol or tetrahydrofuran.

The process for preparing the triazene oxide-platinum complexes is preferably carried out at temperatures of from 0° C. to 50° C., at the pressure of the surrounding atmosphere and with exclusion of light. The organic solvent or the mixture of organic solvent and water is preferably removed after the reaction.

In the following examples unless otherwise mentioned,
(a) all amounts are based on weight;
(b) all pressures are 0.10 MPa (abs.);
(c) all temperatures are 20° C.

All examples worked up to and including Example 6 is carried out with absolute exclusion of light.

GENERAL SYNTHESIS OF TRIAZENE HYDROXIDES USED IN EXAMPLES 1 TO 6

0.1 mole of an aniline derivative is dissolved in 300 ml of 10% strength aqueous hydrochloric acid and cooled to 0° C.

While stirring, 0.1 mole of sodium nitrite dissolved in 40 ml of water, is added slowly. The mixture is subsequently stirred for one hour at 0° C., admixed with 20 g of activated carbon, stirred for a further 10 minutes at 0° C. and then filtered.

The filtrate is then slowly added dropwise to a mixture stirred at 0° C. of 0.1 mole of a hydroxylamine derivative and 0.6 mole of sodium carbonate, dissolved in 600 ml of water. The corresponding triazene hydroxides precipitate from the aqueous solution and are filtered off and carefully washed with water.

The yellow triazene hydroxides are dried to constant weight at room temperature over phosphorus pentoxide in a high vacuum.

The yields are between 50% and 80% of theory.

50 g (1.563 mole) of methanol. A solid precipitates from the methanolic solution and is isolated by filtration. The dark yellow powder is dried to constant weight at room temperature in a high vacuum. This gives 0.84 g of product having a platinum content of 33.8% by weight (yield: 44.1% of theory, based on pure platinum).

0.3 g (0.52 mmol of platinum) of the tetrakis[1-phenyl-3-methyl-3-oxytriaz-1-ene]platinum complex is dissolved in 9.84 g (136.5 mmol) of tetrahydrofuran. The solution contains 1% by weight of pure platinum and is referred to as cat.2.

TABLE 1

| Examples | Aniline derivative | Hydroxylamine derivative | Triazene hydroxide |
|---|---|---|---|
| 1 | $4\text{-NC}-C_6H_4-NH_2$ | $H-NC_6H_{11}(OH).HCl$ | $4\text{-NC}-C_6H_4-N_3C_6H_{11}(OH)$ |
| 2 + 5 | $C_6H_5-NH_2$ | $H-NCH_3(OH).HCl$ | $C_6H_5N_3CH_3(OH)$ |
| 4 + 6 | $4\text{-}CH_3(CH_2)_3-C_6H_4-NH_2$ | $H-NCH_3(OH).HCl$ | $4\text{-}CH_3(CH_2)_3-C_6H_4N_3CH_3-(OH)$ |
| 3 | $4\text{-}CH_3O-C_6H_4-NH_2$ | $H-NCH_3(OH).HCl$ | $4\text{-}CH_3O-C_6H_4N_3CH_3-(OH)$ |

All the following examples were carried out with exclusion of moisture.

EXAMPLES 1 TO 6

Preparation of the triazene oxide-transition metal complexes

Example 1

0.7 g (2.9 mmol) of 1-[4-cyanophenyl]-3-cyclohexyl-3-hydroxytriaz-1-ene are dissolved in 20 g (434.1 mmol) of ethanol.

The solution is subsequently admixed with 0.6 g (3.2 mmol) of a 30% strength methanolic potassium hydroxide solution and stirred for half an hour at room temperature. 0.54 g (1.4 mmol) of cycloocta-1,4-dieneplatinum dichloride, suspended in 10 g (217.1 mmol) of ethanol, are then added slowly and the mixture is stirred for two hours, with a pale beige solid precipitating. The solid is isolated, washed with 10 g of ethanol and dissolved in 30 g (325.6 mmol) of toluene. The solution is filtered and the solvent is evaporated at room temperature in a high vacuum. The residue obtained is 0.8 g of a yellow solid having a platinum content of 28% by weight (yield: 82% of theory; based on pure platinum).

0.3 g (0.43 mmol of platinum) of the bis[1-(4-cyanophenyl)-3-cyclohexyl-3-oxytriaz-1-ene]platinum cycloocta-1,4-diene complex are dissolved in 8.1 g (87.9 mmol) of toluene. The solution contains 1% by weight of pure platinum and is referred to as cat.1.

Example 2

2 g (13.2 mmol) of 1-phenyl-3-methyl-3-hydroxytriaz-1-ene are dissolved in 7 g (97.1 mmol) of tetrahydrofuran. After the solution has been cooled to 0° C., 10 ml (16 mmol of butyllithium) of a 1.6 molar butyllithium solution in n-hexane are slowly added dropwise while stirring, with the temperature not being permitted to exceed 5° C. The reaction mixture is stirred for a further half hour. Subsequently, a solution of 1.11 g (3.3 mmol) of platinum tetrachloride in 15 g (208.0 mmol) of tetrahydrofuran is added slowly at 0° C. while stirring and the reaction solution is stirred for one hour. After filtration, the solvent is evaporated in a high vacuum at room temperature and the residue is taken up in

Example 3

3 g (16.6 mmol) of 1-(4-methoxyphenyl)-3-methyl-3-hydroxy-triaz-1-ene are dissolved in 10 g (138.7 mmol) of tetrahydrofuran. After the solution has been cooled to 0° C., 12.5 ml (20.0 mmol of butyllithium) of a 1.6 molar butyllithium solution in n-hexane are added dropwise while stirring, with the temperature not being permitted to exceed 5° C. The reaction mixture is stirred for a further half hour. Subsequently, a solution of 1.4 g (4.15 mmol) of platinum tetrachloride in 17 g (235.8 mmol) of tetrahydrofuran is added slowly at 0° C. while stirring and the reaction solution is stirred for one hour. After filtration, the solvent is evaporated in a high vacuum at room temperature and the residue is taken up in 50 g (499,2 mmol) of isobutyl methyl ketone. A solid precipitates from the solution and is isolated by filtration. It is washed twice with 20 g (625 mmol) of methanol each time and then dried to constant weight in a high vacuum at room temperature. This gives 1.45 g of a brown powder having a platinum content of 30.4% by weight (yield: 54.4% of theory, based on pure platinum).

0.3 g (0.47 mmol of platinum) of the tetrakis[1-(4-methoxyphenyl)-3-methyl-3-oxytriaz-1-ene]platinum complex is dissolved in 8.82 g (122.3 mmol) of tetrahydrofuran. The solution contains 1% by weight of pure platinum and is referred to as cat.3.

Example 4

3 g (14.5 mmol) of 1-(4-butylphenyl)-3-methyl-3-hydroxy-triaz-1-ene are dissolved in 10 g (138.7 mmol) of tetrahydrofuran. After the solution has been cooled to 0° C., 10.9 ml (17.4 mmol of butyllithium) of a 1.6 molar butyllithium solution in n-hexane are added slowly dropwise while stirring, with the temperature not being permitted to exceed 5° C. The reaction mixture is stirred for a further half hour. Subsequently, a solution of 1.22 g (3.6 mmol) of platinum tetrachloride in 15 g (208.0 mmol) of tetrahydrofuran is added slowly while stirring and the reaction solution is stirred for one hour. After filtration, the solvent is evaporated in a high vacuum at room temperature and the residue is taken up in 50 g (1,563 mol) of methanol. A solid precipitates from the methanolic solution and is isolated by filtration. This is dried to constant weight at room temperature in a high vacuum. This gives 0.72 g of a yellow solid having a platinum content of 30.8% by weight (yield: 31.6% of theory, based on pure platinum).

0.3 g(0.47 mmol of platinum) of the tetrakis[1-(4-butyl-phenyl)-3-methyl-3-oxytriaz-1-ene]platinum complex is dissolved in 8.94 g (97.0 mmol) of toluene. The solution contains 1% by weight of pure platinum and is referred to as cat.4.

Example 5

0.2 g (1.3 mmol) of 1-phenyl-3-methyl-3-hydroxy-triaz-1-ene is dissolved in 2 g (27.7 mmol) of tetrahydrofuran. After the solution has been cooled to 0° C., 1.0 ml (1.6 mmol of butyllithium) of a 1.6 molar butyllithium solution in n-hexane is added slowly dropwise while stirring, with the temperature not being permitted to exceed 5° C. The reaction mixture is stirred for a further half hour.

Subsequently, a solution of 1.2 g (1.3 mmol) of (tris)triphenylphosphine)rhodium chloride in 10 g (138.7 mmol) of tetrahydrofuran is added slowly while stirring at 0° C. and the reaction solution is stirred for one hour. After filtration, the solvent is evaporated in a high vacuum at room temperature and the residue is taken up in 50 g (1.22 mole) of acetonitrile. A solid precipitates from the solution and is isolated by filtration. This is dried to constant weight in a high vacuum at room temperature. This gives 0.31 g of a pale brown powder (yield: 22.9% of theory).

0.1 g (0.096 mmol of rhodium) of the (1-phenyl-3-methyl-3- oxytriaz-1-ene)tris(triphenylphosphine)-rhodium complex is dissolved in 0.89 g (7.5 mmol) of chloroform. The solution contains 1% by weight of pure rhodium and is referred to as cat.5.

Example 6

0.8 g (4.5 mmol) of palladium dichloride is dissolved at 50° C. in 50 g of 5% strength aqueous hydrochloric acid (68.6 mmol of hydrogen chloride). The pH is subsequently adjusted to about 3 using 5.5 g (67.0 mmol) of sodium acetate. Subsequently, a solution of 1.87 g (9.0 mmol) of 1-(4-butylphenyl)- 3-methyl-3-hydroxytriaz-1-ene in 250 g (5.43 mole) of ethanol is added at 60° C. while stirring. A solid precipitates at the beginning of the addition, the amount of solid increasing as the addition of the ethanolic solution progresses. The mixture is then stirred for one additional hour at 60° C., the solid is isolated by filtration and taken up in 70 g (0.76 mole) of toluene. After filtration, the solvent is evaporated at room temperature in a high vacuum and the violet powder is dried to constant weight. This gives 2.1 g of product having a palladium content of 17.8% by weight (yield: 78.1% of theory, based on pure palladium).

0.3 g (0.5 mmol of pure palladium) of the bis[1-(4-butyl-phenyl)- 3-methyl-3-oxytriaz-1-ene]palladium complex is dissolved in 5.04 g (54.7 mmol) of toluene. The solution contains 1% by weight of pure palladium and is referred to as cat.6.

Example 7

0.083 g of cat. 1, whose preparation is described in Example 1, is added to 8 g of α,ω-divinyldimethylpolysiloxane having a viscosity of 500 mPa.s at 25° C. 0.2 g of a copolymer comprising trimethylsiloxane and methylhydrogensiloxane units and having a viscosity of 33 mPa.s at 25° C., which contains 1.12% by weight of Si-bonded hydrogen, is added to the reaction mixture, so that the mixture contains 100 ppm by weight of platinum, calculated as element.

After heating for 4.5 minutes at 50° C., complete crosslinking can be achieved. This gives a transparent product insoluble in organic solvents.

Example 8

The procedure of Example 7 is repeated, except that 0.083 g of cat.4, whose preparation is described in Example 4, is used in place of 0.083 g of cat.1. After 2.2 minutes at 120° C., complete crosslinking can be achieved. This gives a transparent product insoluble in organic solvents.

Example 9

The procedure of Example 7 is repeated, except that the α,ω-divinyldimethylpolysiloxane used has a viscosity of 1000 mPa.s at 25° C. instead of 500 mPa.s at 25° C. and 0.083 g of cat.2, whose preparation is described in Example 2, is used in place of 0.083 g of cat.1.

After 2 minutes at 120° C., complete crosslinking can be achieved. This gives a transparent product insoluble in organic solvents.

Example 10

0.083 g of cat.1, whose preparation is described in Example 1, is mixed into 0.75 g of an organopolysiloxane resin comprising $SiO_2$, trimethylsiloxane, dimethylvinylsiloxane and methylphenylsiloxane units having a viscosity of 1600 mPa.s at 25° C., which contains 7.6% by weight of Si-bonded vinyl groups, 7.45 g of an organopolysiloxane resin comprising $SiO_2$, trimethylsiloxane, dimethylhydrogensiloxane and methylphenylsiloxane units and having a viscosity of 2000 mPa.s at 25° C., which contains 0.2% by weight of Si-bonded hydrogen, are added thereto, so that the mixture contains 100 ppm by weight of platinum After 20 minutes irradiation with ultraviolet light (UVA= 70 mW/cm$^2$ UVB=20 mW/cm$^2$) complete crosslinking of the material is achieved. This gives a pale yellow, transparent product insoluble in organic solvents.

Example 11

The procedure of Example 8 is repeated, except that 0,083 of cat.3, whose preparation is described in Example 3, is used in place of 0,083 g of cat.4.

After 3 minutes irradiation with ultraviolet light (UVA= 70 mW/cm$^2$ UVB=20 mW/cm$^2$) complete crosslinking of the material is achieved. This gives a transparent product insoluble in organic solvents.

Example 12

0.083 g of cat.1, whose preparation is described in Example 1, is added to 7.88 g of α,ω-divinyldimethylpolysiloxane having a viscosity of 500 mPa.s at 25° C. 0.2 g of a copolymer comprising trimethylsiloxane and methylhydrogensiloxane units and having a viscosity of 33 mPa.s at 25° C., which contains 1.12% by weight of Si-bonded hydrogen, and 0.116 g (0.93 mmol) of 1-ethynylcyclohexanol are added to the reaction mixture, so that the mixture contains 100 ppm by weight of platinum, calculated as element.

After 15 seconds irradiation with ultraviolet light (UVA= 70 mW/cm² UVB=20 mW/cm²) complete crosslinking of the material is achieved. This gives a transparent product insoluble in organic solvents.

Example 13

The procedure of Example 7 is repeated, except that 0.083 g of cat.5, whose preparation is described in Example 5, is used in place of 0.083 g of cat.1. After 10 minutes irradiation with ultraviolet light (UVA=70 mW/cm² UVB=20 mW/cm²) complete crosslinking of the material is achieved. This gives a transparent product insoluble in organic solvents.

Example 14

The procedure of Example 10 is repeated, except that 0.083 g of cat.6, whose preparation is described in Example 6, is used in place of 0.083 g of cat.1. After 30 minutes at 170° C., complete crosslinking of the material is achieved. This gives a pale yellow, transparent product insoluble in organic solvents.

What is claimed is:

1. A process comprising reacting organosilicon compounds having Si-bonded hydrogen atoms with organic compounds having aliphatic multiple bonds in the presence of triazene oxide-transition metal complexes of the formula $$M(ANNNOR^1)_a X_b \quad (1)$$

where

M is Pt, Pd, Rh, Ru, Os or Ir,

R¹ is a monovalent, unsubstituted or substituted hydrocarbon radical having from 1 to 18 carbon atoms per radical, a radical of the formula —SiR²$_c$(OR²)$_{3-c}$ or A, R² is identical or different and is an alkyl radical having from 1 to 8 carbon atoms per radical, A is identical or different and is a radical of the formula

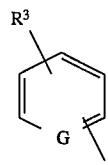

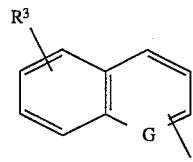

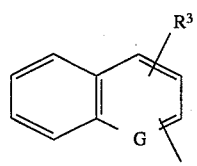

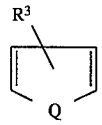

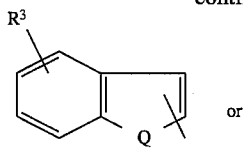

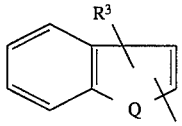

G is CH or N

Q is S, O or NH,

R³ is a monovalent, unsubstituted or substituted hydrocarbon radical having from 1 to 12 carbon atoms per radical or is a radical of the formula —F, —Cl, —Br, —I, —H, —NH₂, —NR²₂, —NO₂, —OH, OR², —SH, —CN, —COOH, —COCl, —CONH₂, —COR², —CHO, —SO₂NHR², —SO₃H, —SO₂Cl or —R⁴—SiR²$_c$(OR²)$_{3-c}$, R⁴ is a divalent hydrocarbon radical having from 1 to 8 carbon atoms per radical, R² is identical or different and is an alkyl radical having from 1 to 8 carbon atoms per radical, X is identical or different and is a ligand selected from the group consisting of Cl, Br, I, NH₃, P(C₂H₅)₃, P(C₆H₅)₃, H, CO, 1,5-cyclooctadiene, pyridine, bipyridine, acetate, acetylacetonate, phenylnitrile, ethylenediamine, acetonitrile, 2,5-norbornadiene, nitrate, nitrite, H₂O, benzene, diphenylphosphinoethane, 1,3-divinyl-1,1,3,3-tetramethyldisiloxane, ethylene and diphenylacetylene, a is 1, 2, 3 or 4, b is 0, or an integer from 1 to 6 and c is 0, 1, 2 or 3, wherein the triazene oxide-transition metal complexes are activated by heating at temperatures of from 50° C. to 250° C. irradiation with light, or by heating and irradiation with light.

2. Crosslinkable organopolysiloxane compositions comprising (1) organopolysiloxanes which have radicals containing aliphatic carbon-carbon multiple bonds, (2) organopolysiloxanes having Si-bonded hydrogen atoms, or in place of organopolysiloxanes (1) and (2)

(3) organopolysiloxanes which have radicals containing aliphatic carbon-carbon multiple bonds and Si-bonded hydrogen atoms, and (4) triazene oxide-transition metal complexes of formula (I) as catalysts.

3. A triazene oxide-platinum complex of the formula $$Pt(ANNNOR^1)_a X_b \quad (VII)$$

where

A is identical or different and is a radical of the formula

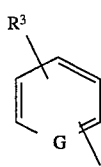

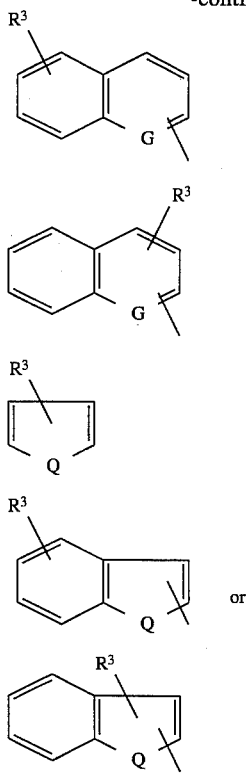

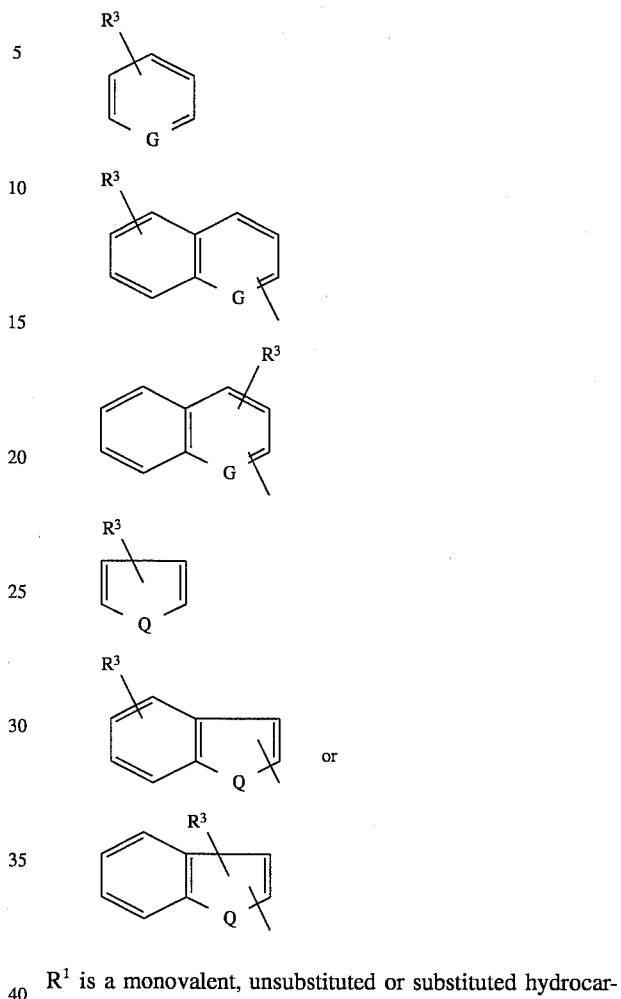

$R^1$ is a monovalent, unsubstituted or substituted hydrocarbon radical having from 1 to 18 carbon atoms per radical, a radical of the formula $-SiR^2_c(OR^2)_{3-c}$ or A, X is identical or different and is a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane, 1,3-divinyl-1,1,3,3-tetramethyldisiloxane, ethylene and diphenylacetylene, a is 1, 2, 3 or 4, and b is 0, or an integer from 1 to 6.

4. A process for preparing triazene oxide-platinum complexes of formula VII, which comprises reacting triazene hydroxides of formula

ANNNOHR$^1$         (VIII), in the presence of bases with platinum compounds of the formula ptX$_d$         (IX), where A is identical or different and is a radical of the formula $R^1$ is a monovalent, unsubstituted or substituted hydrocarbon radical having from 1 to 18 carbon atoms per radical, a radical of the formula $-SiR^2_c(OR^2)_{3-c}$ or A, and X is identical or different and is a ligand selected from the group consisting of Cl, Br, I, $NH_3$, $P(C_2H_5)_3$, $P(C_6H_5)_3$, H CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane, 1,3-divinyl-1,1,3,3-tetramethyldisiloxane, ethylene and diphenylacetylene and d is an integer from 1 to 6.

\* \* \* \* \*